United States Patent [19]
Liu et al.

[11] Patent Number: 5,844,105
[45] Date of Patent: Dec. 1, 1998

[54] PREPARATION OF CRYSTAL FORM II OF CLARITHROMYCIN

[75] Inventors: Jih-Hua Liu, Green Oaks, Ill.; David A. Riley, Kenosha, Wis.

[73] Assignee: Abbott Laboratories, Abbott Park, Ill.

[21] Appl. No.: 681,695

[22] Filed: Jul. 29, 1996

[51] Int. Cl.⁶ .............................. C07G 3/00; C07H 15/00; C07H 17/08; C07H 1/00
[52] U.S. Cl. ........................... 536/18.5; 536/7.2; 536/7.5; 536/124
[58] Field of Search .............................. 536/7.2, 124, 7.5, 536/18.5

[56] References Cited

U.S. PATENT DOCUMENTS

| | | | |
|---|---|---|---|
| 4,331,803 | 5/1982 | Watanabe et al. | 536/7.2 |
| 4,990,602 | 2/1991 | Morimoto et al. | 536/7.4 |

FOREIGN PATENT DOCUMENTS

WO 97/19096  5/1997  WIPO.

OTHER PUBLICATIONS

Quantitative Structure–Activity Relationships In Drug Design, vol. 291 (1989), pp. 325–328, Kim et al., "Conformational Study of Erythromycin Analoques".

Acta Crystallographica, vol. c49, No. 5 (May 1993), pp. 1227–1230, Iwasaki et al., "Structure of 6–0–Methylerythromycin A (Clarithromycin)".

*Primary Examiner*—John Kight
*Assistant Examiner*—Everett White
*Attorney, Agent, or Firm*—Mona Anand

[57] ABSTRACT

The present invention provides a process for the preparation of 6-O-methylerythromycin A Form II comprising converting erythromycin A to 6-O-methylerythromycin A and treating the 6-O-methylerythromycin A with a number of common organic solvents or mixtures of common organic solvents.

16 Claims, 6 Drawing Sheets

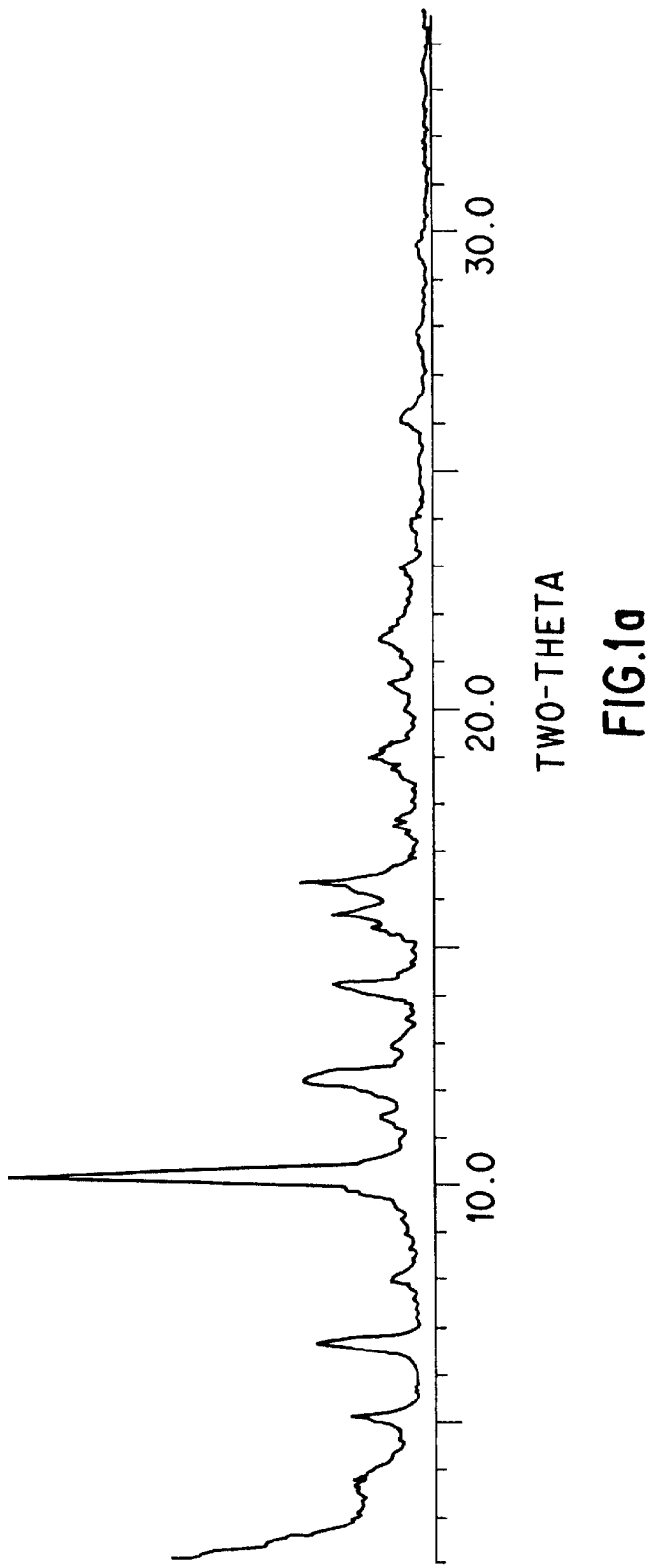

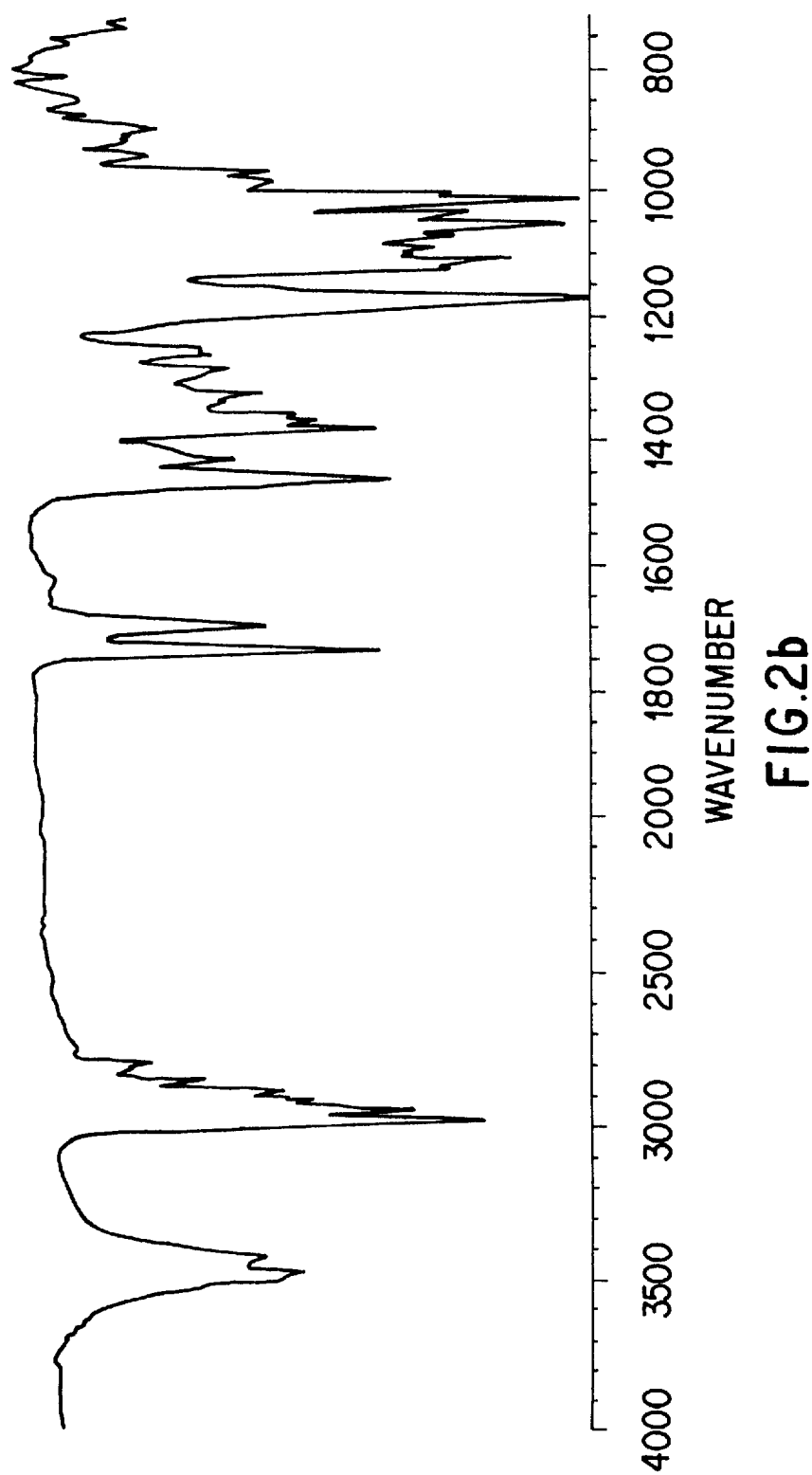

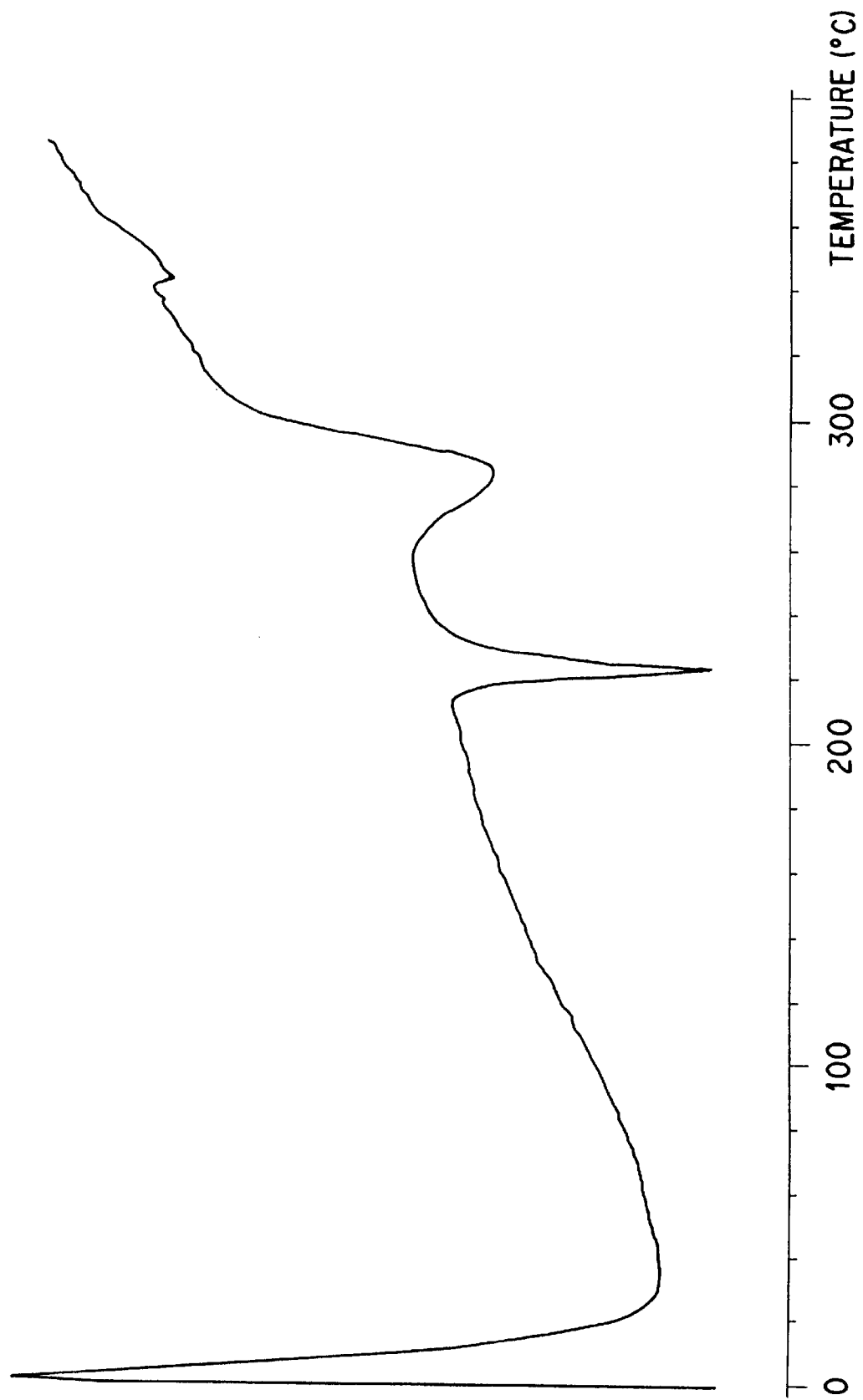

PREPARATION OF CRYSTAL FORM II OF CLARITHROMYCIN

TECHNICAL FIELD

This invention relates to a compound having therapeutic utility and to a method for its preparation. More particularly, the present invention concerns a process for the direct isolation of 6-O-methylerythromycin A crystal form II.

BACKGROUND OF THE INVENTION

6-O-methylerythromycin A (Clarithromycin, Biaxin) is a semisynthetic macrolide antibiotic of formula

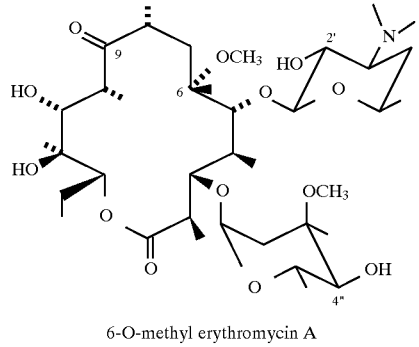

6-O-methyl erythromycin A which exhibits excellent antibacterial activity against gram-positive bacteria, some gram-negative bacteria, anaerobic bacteria, Mycoplasina, and Chlainidia. It is stable under acidic conditions and is efficacious when administered orally. Clarithromycin is a useful therapy for infections of the upper respiratory tract in children and adults.

BRIEF DESCRIPTION OF THE DRAWING

FIGS. 1a, 1b and 1c show, respectively, the powder X-ray diffraction spectrum, the infrared spectrum, and the differential scanning calorimetric (DSC) thermogram of 6-O-methylerythromycin A form I.

FIGS. 2a, 2b and 2c show, respectively, the powder X-ray diffraction spectrum, the infrared spectrum, and the differential scanning calorimetric (DSC) theimogram of 6-O-methylerythromycin A form II.

SUMMARY OF THE INVENTION

Figure 1B:
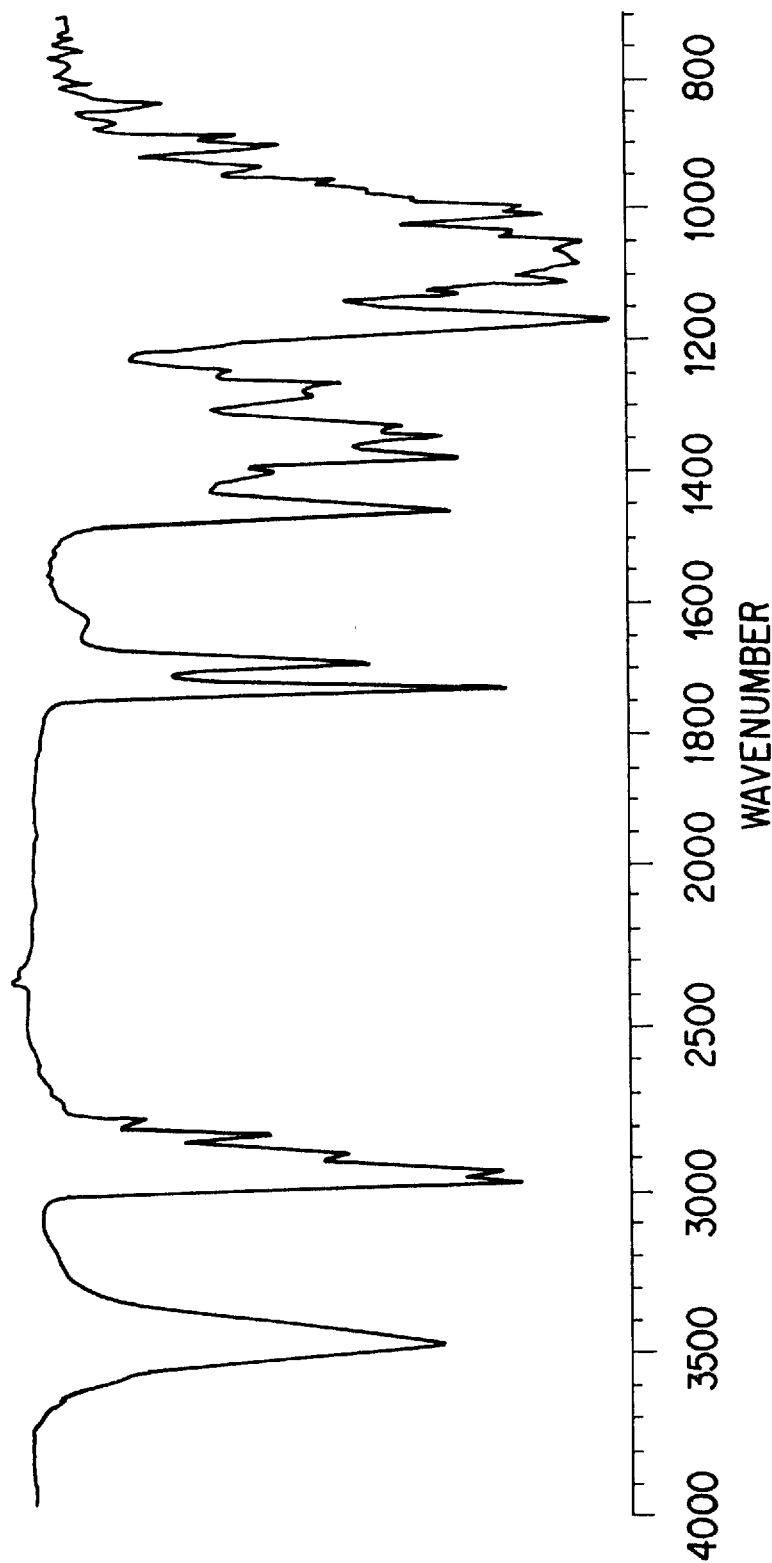
Figure 1C:
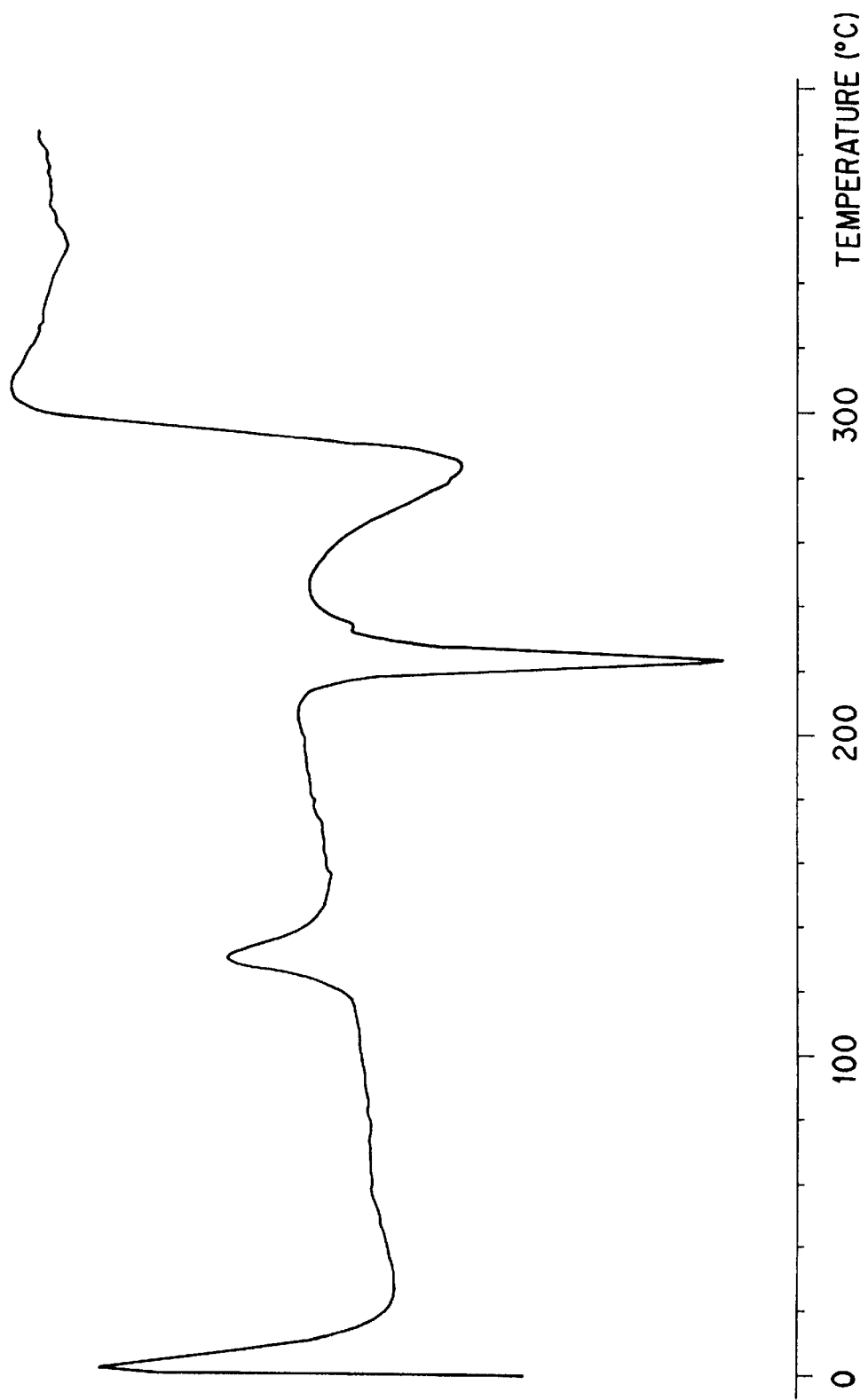
Figure 2A:
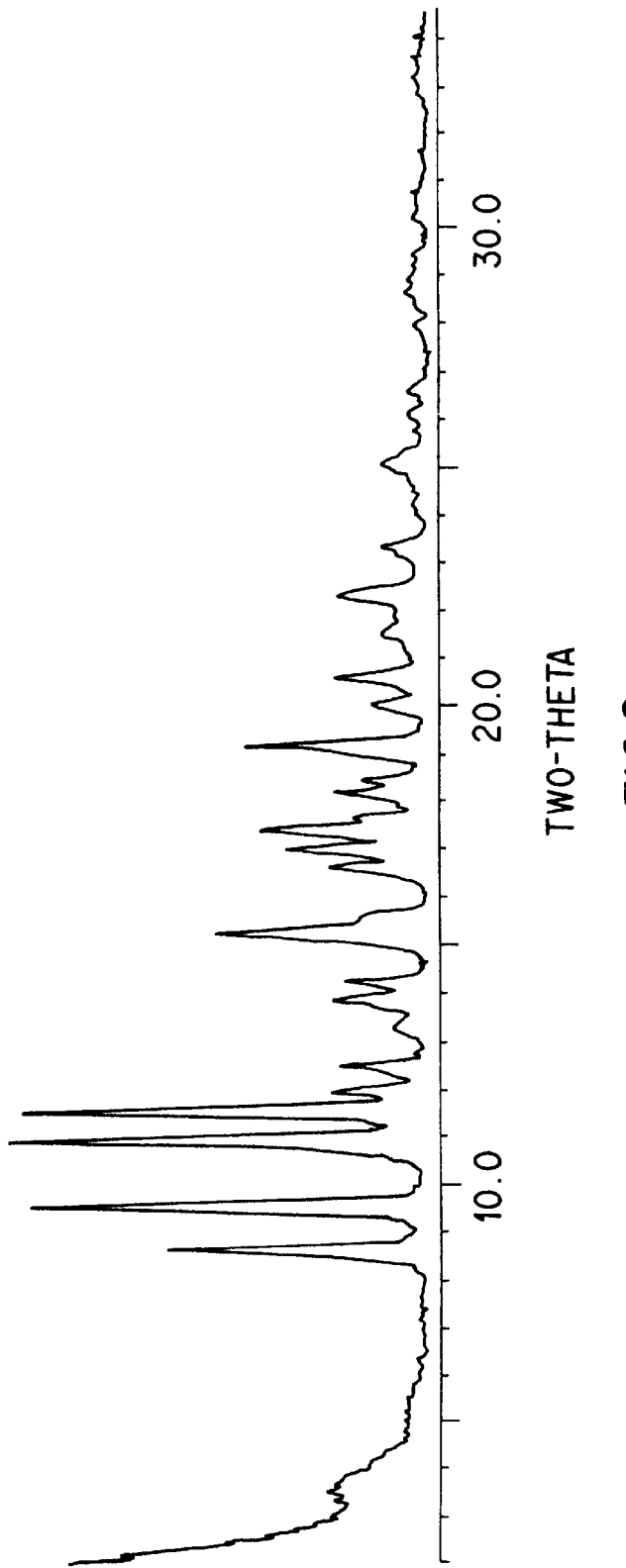

We have discovered that 6-O-methylerythromycin A can exist in at least two distinct crystalline forms, which for the sake of identification are designated "Form I" and "Form II". The crystal forms are identified by their infrared spectrum and powder x-ray diffraction pattern. Investigations in our laboratory have revealed that 6-O-methylerythromycin A prepared by the various methods described in the patent literature summarized below, in which the compound is purified by recrystallization from ethanol, result in exclusive initial formation of crystal form I.

Drugs currently on the market are formulated from the thermodynamically more stable form II. Therefore, preparation of the current commercial entity requires converting the form I crystals to form II. Typically this is done by heating the form I crystals under vacuum at a temperature of greater than 80° C. Therefore, a process for the preparation of 6-O-methylerythromycin A form II which does not require the high temperature treatment would produce substantial processing cost savings.

Although recrystallization from ethanol, tetraliydrofuran, isopropanol or isopropyl acetate results in exclusive formation of form I crystals, 6-O-methylerythromycin A Form II can be isolated directly by using a number of other common organic solvents, or mixtures of common organic solvents, thereby eliminating the additional conversion step.

Accordingly, the present invention provides a process for preparing 6-O-methylerythromycin A Form II comprising (a) converting erythromycin A to 6-O-methylerythromycin A;

(b) treating the 6-O-methylerythromycin A prepared in step (a) with a solvent selected from the group consisting of (i) an alkanol of from 1 to 5 carbon atoms, provided said alkanol is not ethanol or isopropanol, (ii) a hydrocarbon of from 5 to 12 carbon atoms, (iii) a ketone of from 3 to 12 carbon atoms, (iv) a carboxylic ester of from 3 to 12 carbon atoms, provided said carboxylic ester is not isopropyl acetate, (v) an ether of from 4 to 10 carbon atoms, (vi) benzene, (vii) benzene substituted with one or more substituents selected from the group consisting of alkyl of from one to four carbon atoms, alkoxy of from one to four carbon atoms, nitro, and halogen, (viii) a polar aprotic solvent, (ix) a compound having the formula $HNR^1R^2$ wherein $R^1$ and $R^2$ are independently selected from hydrogen and alkyl of one to four carbon atoms, provided that $R^1$ and $R^2$ are not both hydrogen, (x) water and a second solvent selected from the group consisting of a water miscible organic solvent and a water miscible alkanol, (xi) methanol and a second solvent selected from the group consisting of a hydrocarbon of from 5 to 12 carbon atoms, an alkanol of from 2 to 5 carbon atoms, a ketone of from 3 to 12 carbon atoms, a carboxylic ester of from 3 to 12 carbon atoms, an ether of from 4 to 10 carbon atoms, benzene, and benzene substituted with one or more substituents selected from the group consisting of alkyl of from one to four carbon atoms, alkoxy of from one to four carbon atoms, nitro, and halogen, and (xii) a hydrocarbon of from 5 to 12 carbon atoms and a second solvent selected from the group consisting of a ketone of from 3 to 12 carbon atoms, a carboxylic ester of from 3 to 12 carbon atoms, an ether of from 4 to 10 carbon atoms, benzene, benzene substituted with one or more substituents selected from the group consisting of alkyl of from one to four carbon atoms, alkoxy of from one to four carbon atoms, nitro, and halogen, and a polar aprotic; and (c) isolating the 6-O-methylerythromycin A form II crystals.

DETAILED DESCRIPTION

6-O-methylerythromycin A is prepared by methylation of the 6-hydroxy group of erythromycin A. However, in addition to the 6 position, erythromycin A contains hydroxy groups at the 11, 12, 2' and 4" positions, and a nitrogen at 3' position, all of which are potentially reactive with alkylating agents. Therefore, it is necessary to protect the various reactive functionalities prior to alkylation of the 6-hydroxy group. Representative 6-O-methylerythromycin A preparations are described in U.S. Pat. Nos. 4,331,803, 4,670,549, 4,672,109 and 4,990,602 and European Patent Specification 260 938 B 1 which are incorporated herein by reference. Following final removal of the protecting groups, the 6-O-methylerythromycin A may exist as a solid, a semisolid, or a syrup containing residual solvents from the deprotection reactions, inorganic salts, and other impurities. 6-O-methylerythromycin A form II may be crystallized directly from the syrup or semisolid using the solvent systems described above. Alternatively, if the crude reaction product solidifies, the solid may be recrystallized from any of the solvent systems described above. Pure 6-O-methylerythromycin A form II may also be obtained by recrystallizing form I or mixtures of form I and form II from any of the solvent systems described above. The term "6-O-methylerythromycin A" as used herein is meant to include 6-O-methylerythromycin A Form I or II in any state of purity, or mixtures thereof.

The term "treating" refers to crystallizing or recrystallizing 6-O-methylerythromycin A as defined above from any of the solvent systems described above.

The term "hydrocarbon" as used herein refers to straight chain or branched alkanes having the formula $C_nH_{2n+2}$. Hydrocarbons suitable for use in isolating 6-O-methylerythromycin A form II crystals include hexane, heptane, octane and the like.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "ketone" refers to a solvent of formula RC(O)R' where R and R' are straight or branched alkyl. Ketones suitable for use in isolating 6-O-methylerythromycin A form II crystals include acetone, methyl ethyl ketone, 2-, and 3-pentanone, and the like.

The term "carboxylic ester" means a solvent of formula $RCO_2R'$ where R and R' are straight or branched alkyl. Carboxylic esters suitable for use in isolating 6-O-methylerythromycin A form II crystals include methyl acetate, ethyl acetate, isobutyl acetate, and the like.

The term "ether" means a solvent of formula ROR' where R and R' are straight or branched alkyl. Ethers suitable for use in isolating 6-O-methylerythromycin A form II crystals include ethyl ether, diisopropyl ether, methyl tert-butyl ether, and the like.

The term "polar aprotic" refers to solvents which do not contain hydroxy groups but have a relatively high dipole moment. Polar aprotic solvents suitable for use in isolating 6-O-methylerythromycin A form II crystals include acetonitrile, N,N-dimethylformamide (DMF), dimethyl sulfoxide (DMSO), 1,1-dimethoxyethane (DME), hexamethylphosphoric triamide (HMPA), and the like.

The term "water miscible organic solvents" means organic solvents which are substantially miscible with water. Examples of water miscible organic solvents suitable for use in isolating 6-O-methylerythromycin A form II crystals from water miscible organic solvent-water mixtures include acetone, acetonitrile, N,N-dimethylformamide (DMF), dimethyl sulfoxide (DMSO), tetrahydrofuran, dioxane, ethylene glycol diethyl ether, ethylene glycol dimethyl ether (glyme), and diethylene glycol dimethyl ether (diglyme).

The term "alkanol" refers to a hydrocarbon as defined above substituted with one or more hydroxy groups. Representative alkanols include methanol, propanol, isopropanol, butanol, isobutanol, ethylene glycol, and the like.

The term "water miscible alkanols" means an alkanol as defined above which is substantially miscible with water. Examples of water miscible alkanols suitable for use in isolating 6-O-methylerythromycin A form II crystals from water miscible alkanol-water mixtures include methanol, ethanol, propanol, isopropanol, butanol, isobutanol and tert-butanol. 6-O-methylerythromycin A is prepared from erythromycin A by a variety of synthetic routes. In one method, erythromycin A is converted to 2'-O-3'-N-bis(benzyloxycarbonyl)-N-

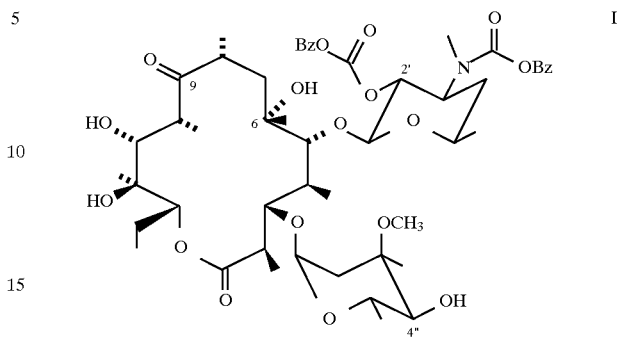

demethylerythromycin A (I). The 6-hydroxy group is then methylated by reaction with an alkylating agent such as bromomethane or iodomethane and a base. Removal of the benzoyl groups by catalytic hydrogenation and reductive methylation of the 3' N gives 6-O-methylerythromycin A. See U.S. Pat. No. 4,331,803.

An alternative synthetic route involves methylation of 6-O-methylerythromycin A-9-oxime. 6-O-methylerythromycin A-9-oxime is prepared by methods well known in the art such as reaction of erythromycin A with hydroxylamine hydrochloride in the presence of base, or by reaction with hydroxylamine in the presence of acid as described in U.S. Pat. No. 5,274,085. Reaction of the oxime with RX wherein R is allyl or benzyl and X is halogen results in formation of 2'-O,3'-N-diallyl or dibenzylerythromycin A-9-O-allyl or benzyloxime halide. Methylation of this quarternary salt as described above, followed by elimination of the R groups and deoxmimation gives 6-O-methylerythromycin A. See U.S. Pat. No. 4,670,549.

Methylation of 6-O-methylerythromycin A oxime derivatives of formula II,

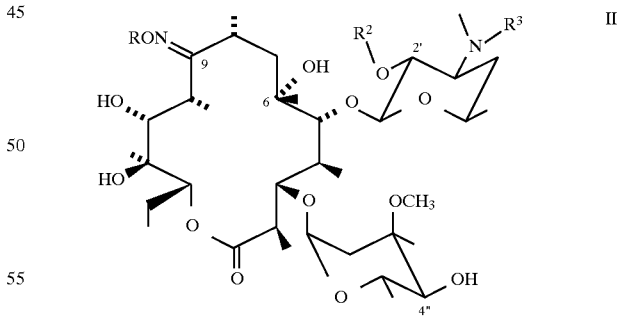

wherein R is alkyl, alkenyl, substituted or unsubstituted benzyl, oxyalkyl, or substituted phenylthioalkyl, $R^2$ is benzoyl, and $R^3$ is methyl or benzoyl, followed by deprotection, deoximation, and reductive methylation when $R^3$ is benzoyl gives 6-O-methylerythromycin A. See U.S. Pat. Nos. 4,672,109.

A particularly useful preparation of 6-O-methylerythromycin A involves methylation of the

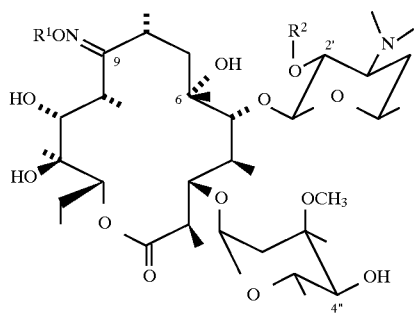

oxime derivative III, wherein $R^1$ is alkenyl, substituted or unsubstituted benzyl, or alkoxyalkyl, $R^2$ is substituted silyl, and $R^3$ is $R^2$ or H. Removal of the protecting groups and deoximation is then accomplished in a single step by treatment with acid to give 6-O-methylerythromycin A. See European Patent Specification 260 938 B 1 and U.S. Pat. No. 4,990,602.

A preferred route of 6-O-methylerythromycin A is outlined in Scheme 1. Erythromycin A, prepared by fermentation of *Streptomyces erythreus* is oximated to give oxime 4 wherein $R^1$ is alkoxyalkyl. The group $R^1$ may be introduced by reaction of erythromycin A with the substituted hydroxylamine $R^1ONH_2$, or by reaction of erythromycin A with hydroxylamine hydrochloride in the presence of base, or hydroxylamine in the presence of acid, followed by reaction with $R^1X$. The two hydroxy groups are then protected simultaneously, in which $R^2$ or $R^3$ are the same, or sequentially in which $R^2$ and $R^3$ are different. Particularly useful protecting groups are substituted silyl groups such as trimethylsilyl, tert-butyldimethylsilyl, tert-butyldiphenylsilyl and the like. The protecting groups are then removed and the compound is deoximated to produce 6-O-methylerythromycin A. The order of deprotection/deoximation is not critical. When the protecting groups are substituted silyl, deprotection and deoximation can be accomplished in a single step by treatment with acid, for example using formic acid or sodium hydrogen sulfite. See U.S. Pat. No. 4,990,602.

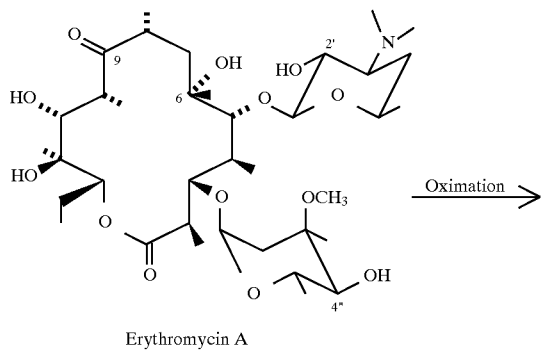

The 6-O-methylerythromycin A prepared as described above is suspended in the desired solvent and heated to about the reflux temperature of the solvent. Heating is then continued and the suspension is stirred for an amount of time sufficient to dissolve most of the solid, generally about 10 minutes to 2 hours. The suspension is then filtered hot. If necessary, the filtrate may be heated to at or about the reflux temperature of the solvent to form a clear solution. The filtrate is then slowly cooled to ambient temperature with optional further cooling in an ice-water bath. For purposes of this specification, ambient temperature is from about 20° to about 25° C. 6-O-methylerythromycin A crystal form II is isolated by filtration and dried in a vacuum oven at a temperature of between ambient temperature and about 50° C., and a pressure of between about 2 inches of mercury and atmospheric pressure to remove any remaining solvent.

When 6-O-methylerythromycin A is treated with a water miscible organic solvent and water or a water miscible alkanol and water, a suspension of 6-O-methylerythromycin A in the organic solvent or alkanol is heated to reflux and hot filtered. If necessary, the filtrate is heated at about the reflux temperature of the solvent until a clear solution is obtained. The clear solution is then mixed with water and cooled to ambient temperature with optional further cooling in an ice bath. The upper limit on the amount of water occurTs when the mixture separates into two liquid phases. A preferred ratio is about 1:1 parts by volume of water. After cooling, 6-O-methylerythromycin A crystal form II is isolated by filtration and dried as described above. A preferred water miscible organic solvent is tetrahydrofuran. Preferred water miscible alkanols include methanol, ethanol, propanol and isopropanol.

In another aspect of the present invention, 6-O-methylerythromycin A may is treated with mixtures of methanol and a second solvent. In this case, the second solvent my include solvents such as ethanol, isopropanol, tetrahydrofuran or isopropyl acetate which normally result in formation of form I crystals. Because the drug may have comparable solubilities in methanol and the second solvent, the amount of methanol must be carefully controlled to ensure maximum recovery. Preferred amounts of methanol are from about 1:3 to about 1:1 parts by volume. An especially preferred ratio is about 1:1 parts by volume of methanol. In accordance with this aspect of the invention, a suspension of 6-O-methylerythromycin A in the second solvent is heated to reflux and hot filtered. If necessary, the filtrate is heated at about the reflux temperature of the second solvent until a clear solution is obtained. The hot solution is then mixed with methanol and cooled to ambient temperature with optional further cooling in an ice bath. Alternatively, when 6-O-methylerythromycin A has comparable solubility in both the second solvent and methanol, the second solvent and methanol are premixed in a ratio of about 1:1 parts by volume and the drug is suspended in a the solvent mixture, followed by heating, filtration, and cooling as described above. After cooling, 6-O-methylerythromycin A crystal form II is isolated by filtration and dried as described above.

In accordance with the aspects of this invention wherein 6-O-methylerythromycin A is treated with hydrocarbon-second solvent mixtures, 6-O-methylerythromycin A is suspended in the desired second solvent and heated to about the reflux temperature of the second solvent The suspension is then heated and stirted for an amount of time sufficient to dissolve most of the solid, generally about 10 minutes to 2 hours. The suspension is then filtered hot. The filtrate may be heated to reflux to form a clear solution if necessary. A hydrocarbon solvent is then added to the hot filtrate and the mixture is cooled slowly to ambient temperature with optional further cooling in an ice bath. After cooling, 6-O-methylerythromycin A crystal form II is isolated by filtration and dried as described above. The amount of hydrocarbon solvent added is dependent on the solubility of the drug in the second solvent and the hydrocarbon solvent, and can be readily determined by one of ordinary skill in the art. Typical ratios fall in the range of about 1:10 to about 1:1 parts by volume of hydrocarbon solvent.

In a preferred embodiment, 6-O-methylerythromycin A crystal form II is isolated by treating 6-O-methylerythromycin A with a solvent selected from the group consisting of acetone, heptane, toluene, methyl tert-butyl ether, N,N-dimethylformamide, ethyl acetate, xylene, ethyl ether, amyl acetate, diisopropyl ether, and isopropyl butyrate.

In a more preferred embodiment, 6-O-methylerythromycin A crystal form II is isolated by treating 6-O-methylerythromycin A with water and a solvent selected from the group consisting of a water miscible organic solvent and a water miscible alkanol. An especially preferred water miscible organic solvent is tetrahydrofuran. Especially preferred water miscible alkanols are methanol, ethanol, propanol, and isopropanol.

When water is replaced with methanol in solvent mixtures, drying times are shortened or drying can be accomplished at a lower temperature. Therefore, in a still more preferred embodiment, 6-O-methylerythromycin A crystal form II is isolated by treating 6-O-methylerythromycin A with a solvent comprising methanol and a second solvent selected from the group consisting of a hydrocarbon of from 5 to 12 carbon atoms, an alkanol of from 2 to 5 carbon atoms, a ketone of from 3 to 12 carbon atoms, a carboxylic ester of from 3 to 12 carbon atoms, an ether of from 4 to 10 carbon atoms, benzene, and benzene substituted with one or more substituents selected from the group consisting of alkyl of from one to four carbon atoms, alkoxy of from one to four carbon atoms, nitro, and halogen. Preferred solvents according to this embodiment are methanol and alkanols of from 2 to 5 carbon atoms, and methanol and carboxylic esters of from 3 to 12 carbon atoms. Especially preferred solvents are methanol-ethanol and methanol-isopropyl acetate.

In the most preferred embodiment of the present invention, 6-O-methylerythromycin A crystal form II is isolated by treating 6-O-methylerythromycin A with a solvent having the formula $HNR^1R^2$ wherein $R^1$ and $R^2$ are independently selected from hydrogen and alkyl of one to four carbon atoms, provided that $R^1$ and $R^2$ are not both hydrogen. Alkyl and dialkylamines are preferred because 6-O-methylerythromycin A is substantially soluble in these solvents and the solvents are readily evaporated, resulting in lower solvent and energy costs. The most preferred solvent is isopropylamine.

The foregoing may be better understood by reference to the following examples which are provided for illustration and not intended to limit the scope of the inventive concept.

REFERENCE EXAMPLE

6-O-methylerythromycin A was prepared from erythromycin A by oximation of the C-9 carbonyl, protection of the C-2' and C-4" hydroxy groups, methylation of the C-6 hydroxy group, deoximation and removal of the protecting groups, and recrystallization from ethanol according to the method of U.S. Pat. No. 4,990,602 to give 6-O-methylerythromycin A form I. The form I crystals (0.40 g) were placed in a vial and heated in the vacuum oven (4–9 in Hg, 100°–110° C.) for 18 hours to give 6-O-methylerythromycin A form II crystals.

6-O-methylerythromycin A form II melts at 223.4° C. In the differential scanning calorimetric thermogram of 6-O-methylerythromycin A form II there can be seen an endothermic peak at 283.3° C. which may be due to decomposition. After the DSC scan the color of the sample was black. The 2-theta angle positions in the powder x-ray diffraction pattern of 6-O-methylerythromycin A form I are 8.52°±0.2, 9.48°±0.2, 10.84°±0.2, 11.48°±0.2, 11.48°±0.2, 12.36°±0.2, 13.72°±0.2, 14.12°±0.2, 15.16°±0.2, 16.48°±0.2, 16,92°±0.2, 17.32°±0.2, 18.08°±0.2, 18.40°±0.2, 19.04°±0.2, 19.88°±0.2, and 20.48°±0.2.

EXAMPLE 1

Recrystallization from Acetone

A suspension of 6-O-methylerythromycin A (30 g) in acetone (200 mL) was heated at reflux for 15 minutes. The hot solution was filtered and 5.53 g of solid was removed. The filter flask was rinsed with acetone (5 mL). The combined filtrate and rinse was warmed to reflux and acetone (45 mL) was added to dissolve all remaining solid. The solution was cooled to ambient temperature and then in an ice-water bath. The resulting solid was filtered and dried overnight in a vacuum oven (4–9 in Hg, 40°–45° C.) to give 6-O-methylerythromycin A form II (17.8 g).

EXAMPLE 2

Recrystallization from Heptane

A suspension of 6-O-methylerythromycin A (10 g) in heptane (1000 mL) was heated at reflux (98° C.) for 1.5 hours. The hot solution was filtered and 1.91 g of solid was removed. The filtrate was warmed to reflux and heated for 35 minutes. The clear solution was cooled to ambient temperature and then in an ice-water bath. The resulting solid was filtered and dried overnight in a vacuum oven (4–9 in Hg, 40°–45° C.) to give 6-O-methylerythromycin A form II (5.7 g).

EXAMPLE 3

Recrystallization from Toluene

A suspension of 6-O-methylerythromycin A (30 g) in toluene (100 mL) was heated at reflux (110°–112° C.) for 1.5 hours. The hot solution was filtered and the filter flask was rinsed with toluene (10 mL). The combined filtrate and rinse was warmed to reflux (110° C.) and heated for 35 minutes. The solution was cooled to ambient temperature and then in an ice-water bath. The resulting solid was filtered and dried overnight in a vacuum oven (4–9 in Hg, 40°–45° C.) to give 6-O-methylerythromycin A form II (5.7 g).

EXAMPLE 4

Recrystallization from Methyl tert-Butyl Ether

A suspension of 6-O-methylerythromycin A (10 g) in methyl tert-butyl ether (200 mL) was heated at reflux (55° C.) for 15 minutes. The hot solution was filtered and 2.6 g of solid was removed. The filtrate was warmed to reflux and methyl tert-butyl ether (70 mL) was added to dissolve the remaining solid. The solution was cooled to ambient temperature and then in an icewater bath. The resulting solid was filtered and dried overnight in a vacuum oven (4–9 in Hg, 40°–45° C.) to give 6-O-methylerythromycin A form II (4.6 g).

EXAMPLE 5

Recrystallization from N,N-Dimethylformamide

A suspension of 6-O-methylerythromycin A (20 g) in N,N-dimethylformamide (200 mL) was heated at reflux (153° C.) for 15 minutes. The hot solution was filtered and the filtrate was warmed to reflux. The clear solution was cooled slowly to ambient temperature and stirred for four days. The resulting solid was filtered and dried overnight in a vacuum oven (4–9 in Hg, 40°–45° C.) to give 6-O-methylerythromycin A form II (7.4 g).

EXAMPLE 6

Recrystallization from Ethyl Acetate

A suspension of 6-O-methylerythromycin A (15 g) in ethyl acetate (100 mL) was heated at reflux (77° C.) for 30 minutes. The hot solution was filtered and the filtrate was warmed to reflux. To the cloudy solution was added ethyl acetate (15 mL). The resulting clear solution was cooled to ambient temperature overnight. The resulting solid was filtered and dried in a vacuum oven (4–9 in Hg, 40°–45° C.) for 91 hours to give 6-O-methylerythromycin A form II (8.7 g).

EXAMPLE 7

Recrystallization from Xylene

A suspension of 6-O-methylerythromycin A (35 g) in xylene (105 mL) was heated to 140° C. at which point a clear solution was obtained. Additional 6-O-methylerythromycin A (5.0 g) was added and the hot solution was filtered to remove a trace amount of insoluble material. The filter flask was rinsed with xylene (5 mL) and the combined filtrate and rinse were heated at reflux for 15 minutes. The solution was cooled to ambient temperature and then in an ice water bath. The resulting solid was filtered and dried overnight in a vacuum oven (4–9 in Hg, 40°–45° C.) to give 6-O-methylerythromycin A form II (29 g).

EXAMPLE 8

Recrystallization from Isopropanol-Water

A suspension of 6-O-methylerythromycin A (20 g) and isopropanol (100 mL) was heated to reflux (82° C.). The hot solution was filtered and 1.16 g of solid was removed. The filtrate was diluted with isopropanol (20 mL) and was again warmed to reflux. The hot suspension was filtered and 3.5 g of 6-O-methylerythromycin A was collected. To the filtrated was added isopropanol (50 mL) and the mixture was heated at reflux until a clear solution was obtained. To the clear solution was added water (100 mL) and the solution was cooled in an ice bath. The resulting solid was filtered and dried overnight in a vacuum oven (4–9 in Hg, 40°–45° C.) to give 6-O-methylerythromycin A form II (9.5 g).

EXAMPLE 9

Recrystallization from Tetrahydrofuran-Water

A suspension of 6-O-methylerythromycin A (30 g) in THF (100 mL) was heated at reflux (66.5° C.) for 20 minutes. The hot solution was filtered to remove a trace amount of insoluble material. The filtrate was warmed to (66.5° C.) and water (100 mL) was added at which point a solid formed. The suspension was cooled to ambient temperature and filtered. The solid was dried in a vacuum oven (4–9 in Hg, 40°–45° C.) for four days to give 6-O-methylerythromycin A form II (24 g).

EXAMPLE 10

Recrystallization from Ethanol-Water

A suspension of 6-O-methylerythromycin A (20 g) in ethanol (200 mL) was heated to 78° C. The hot solution was filtered and 12.6 g of solid was removed. The filtrate was warmed to reflux and water (200 mL) was added. The mixture was cooled to ambient temperature and filtered. The solid was dried in a vacuum oven (4–9 in Hg, 40°–45° C.) to give 6-O-methylerythromycin A form II (8.8 g).

EXAMPLE 11

Recrystallization from Ethyl Ether

A suspension of 6-O-methylerythromycin A (5.0 g) in ethyl ether (150 mL) was warmed to reflux. The insoluble solids were removed by filtration and the filtrate was cooled to ambient temperature. A precipitate slowly appeared and was isolated by filtration to give 6-O-methylerythromycin A form II (0.8 g). The filtrate was stirred overnight at ambient temperature to give an additional 0.65 g of 6-O-methylerythromycin A form II.

EXAMPLE 12

Recrystallization from Amyl Acetate

A suspension of 6-O-methylerythromycin A in amyl acetate (100 mL) was warmed 93° C. at which point the solution was almost clear. A trace amount of insoluble solids were removed by filtration of the hot solution and the filtrate was cooled to ambient temperature. A precipitate slowly appeared and was isolated by filtration to give 6-O-methylerythromycin A form II (6.9 g) after drying overnight at ambient temperature (4–9 in Hg).

EXAMPLE 13

Recrystallization from Isopropyl Acetate-Methanol

A suspension of 6-O-methylerythromycin A (12 g) in isopropyl acetate (100 mL) was warmed to reflux. The hot solution was filtered and the filtrate was transferred to another vessel. The filter flask was rinsed with isopropyl acetate (10 mL) and the combined filtrate and rinse were warmed to reflux. Methanol (100 mL) was added and the clear solution was cooled slowly to ambient temperature during which time a precipitate formed. After three hours at ambient temperature the precipitate was collected by filtration. The soid was dried in a vacuum oven (4–9 in Hg, 40°–45° C.) to give 6-O-methylerythromycin A form II (6.8 g).

EXAMPLE 14

Recrystallization from Diisopropyl Ether

A suspension of 6-O-methylerythromycin A (3.0 g) and diisopropyl ether (150 mL) was warmed to reflux. The hot solution was filtered rapidly and the filtrate was cooled to ambient temperature over two hours. The resulting solid was collected by filtration and dried in the vacuum oven (7–9 in Hg, 45°–50° C.) to give 6-O-methylerythromycin A form II (0.27 g).

EXAMPLE 15

Recrystallization from Isopropyl Butyrate

A suspension of 6-O-methylerythromycin A (5.0 g) in ispropyl butyrate (100 mL) was warmed to 90° C. The resulting clear solution was cooled to ambient temperature over three hours and then was cooled for 30 minutes in an ice-water bath. The resulting solid was collected by filtration and dried in the vacuum oven (2–4 in Hg, 45°–50° C.) to give 6-O-methylerythromycin A form II (2.8 g).

EXAMPLE 16

Recrystallization from Isopropylamine

A clear solution resulting from addition of 6-O-methylerythromycin A (8.0 g) to isopropylamine (50 mL) was stirTed overnight at ambient temperature. When no precipitate formed, and additional 10.4 g of 6-O-methylerythromycin A was added. The clear solution was stirred oveinight at ambient temperature duiing which time a precipitate formed. The solid was collected by filtration and dried in the vacuum oven (2–4 in Hg, 45°–50° C.) to give 6-O-methylerythromycin A form II (16.2 g).

EXAMPLE 17

Recrystallization from Methanol-Ethanol

A mixture of 6-O-methylerythromycin A (15 g).ethanol (100 mL) and methanol (100 mL) was warmed to 69° C. and stirred for 30 minutes. The hot solution was filtered and the filtrate was transferred to another vessel. The clear solution was cooled to ambient temperature over two hours and then was stirred for 30 minutes in an ice-water bath. The resulting solid was collected by filtration and dried in the vacuum oven (2–4 in Hg, 45°–50° C.) to give 6-O-methylerythromycin A form II (7.1 g).

The foregoing examples are presented for purposes of illustration and are not intended to limit the scope of the invention. Vaiiations and changes which are obvious to one skilled in the art are intended to be within the scope and nature of the invention as defined in the appended claims.

We claim:

1. A method of preparing 6-O-methylerythromycin A crystal form II comprising
   (a) converting erythromycin A to 6-O-methylerythromycin A;
   (b) treating the 6-O-methylerythromycin A prepared in step a with a solvent selected from the group consisting of
      (i) an alkanol of from 1 to 5 carbon atoms, provided said alkanol is not ethanol or isopropanol,
      (ii) a hydrocarbon of from 5 to 12 carbon atoms,
      (iii) a ketone of from 3 to 12 carbon atoms,
      (iv) a carboxylic ester of from 3 to 12 carbon atoms, provided said carboxylic ester is not isopropyl acetate,
      (v) an ether of from 4 to 10 carbon atoms,
      (vi) benzene,
      (vii) benzene substituted with one or more substituents selected from the group consisting of
         alkyl of from one to four carbon atoms,
         alkoxy of from one to four carbon atoms,
         nitro, and
         halogen,
      (viii) a polar aprotic solvent,
      (ix) a compound having the formula $HNR^1R^2$ wherein $R^1$ and $R^2$ are independently selected from hydrogen and alkyl of one to four carbon atoms, provided that $R^1$ and $R^2$ are not both hydrogen,
      (x) water and a water miscible solvent selected from the group consisting of
         a water miscible organic solvent and
         a water miscible alkanol,
      (xi) methanol and a second solvent selected from the group consisting of a hydrocarbon of from 5 to 12 carbon atoms,
an alkanol of from 2 to 5 carbon atoms,
a ketone of from 3 to 12 carbon atoms,
a carboxylic ester of from 3 to 12 carbon atoms,
an ether of from 4 to 10 carbon atoms,
benzene, and
benzene substituted with one or more substituents selected from the group consisting of
alkyl of from one to four carbon atoms,
alkoxy of from one to four carbon atoms,
nitro, and
halogen, and (xii) a hydrocarbon of from 5 to 12 carbon atoms and a second solvent selected from the group consisting of
a ketone of from 3 to 12 carbon atoms,
a carboxylic ester of from 3 to 12 carbon atoms,
an ether of from 4 to 10 carbon atoms,
benzene,
benzene substituted with one or more substituents selected from the group consisting of
alkyl of from one to four carbon atoms,
alkoxy of from one to four carbon atoms,
nitro, and
halogen, and
a polar aprotic; and (c) isolating the 6-O-methylerythromycin A form II crystals.

2. The process of claim 1 wherein step (a) comprises
(i) converting erythromycin A into an erythromycin A 9-oxime derivative;
(ii) protecting the 2' and 4" hydroxy groups of the erythromycin A 9-oxime derivative prepared in step (i);
(iii) reacting the product of step (ii) with a methylating agent; and
(iv) deprotecting and deoximating the product of step (iii) to form 6-O-methylerythromycin A.

3. A method according to claim 2 wherein the solvent comprises water and a water miscible organic solvent or a water miscible alkanol.

4. A method according to claim 3 wherein the solvent comprises water and a water miscible organic solvent or water miscible alkanol in a ratio of about 1:1 parts by volume.

5. A method according to claim 4 wherein the solvent comprises water and a water miscible organic solvent.

6. A method of preparing 6-O-methylerythromycin A crystal foim II according to claim 5 wherein water miscible organic solvent is tetrahydrofuran.

7. A method according to claim 4 wherein the solvent comprises water and a water miscible alkanol.

8. A method according to claim 7 wherein the water miscible alkanol is selected from the group consisting of methanol, ethanol, and isopropanol.

9. A method of according to claim 2 wherein the solvent comprises methanol and a second solvent selected from the group consisting of a hydrocarbon of from 5 to 12 carbon atoms,
an alkanol of from 2 to 5 carbon atoms,
a ketone of from 3 to 12 carbon atoms,
a carboxylic ester of from 3 to 12 carbon atoms,
an ether of from 4 to 10 carbon atoms,
benzene, or
benzene substituted with one or more substituents selected from the group consisting of
alkyl of from one to four carbon atoms,
alkoxy of from one to four carbon atoms,
nitro, and
halogen.

10. A method according to claim 9 wherein the solvent comprises methanol and
an alkanol of from 2 to 5 carbon atoms, or
a carboxylic ester of from 3 to 12 carbon atoms.

11. A method according to claim 10 wherein the solvent comprises methanol and an alkanol of from 2 to 5 carbon atoms, or a carboxylic ester of from 3 to 12 carbon atoms in a ratio of about 1:1 parts by volume.

12. A method according to claim 11 wherein the solvent comprises methanol and a second solvent selected from ethanol and isopropyl acetate.

13. A method according to claim 2 wherein the solvent comprises a compound of formula $HNR^1R^2$ wherein $R^1$ and $R^2$ are independently selected from hydrogen and alkyl of one to four carbon atoms, provided that $R^1$ and $R^2$ are not both hydrogen.

14. A method according to claim 13 wherein the solvent is isopropylamine.

15. A method according to claim 2 wherein the solvent is selected from the group consisting of
acetone,
heptane,
toluene,
methyl tert-butyl ether,
N,N-dimethylformamide,
ethyl acetate,
xylene,
isopropanol-water,
tetrahydrofuraii-water,
ethanol-water,
ethyl ether,
amyl acetate,
isopropyl acetate-methanol
diisopropyl ether,
isopropyl butyrate,
isopropylamine, and
methanol-ethanol.

16. 6-O-methylerythromycin A form II prepared according to the process of claim 2.

* * * * *